(12) United States Patent
Lihl et al.

(10) Patent No.: US 6,308,877 B1
(45) Date of Patent: *Oct. 30, 2001

(54) DEVICE FOR FORMING TRIANGULAR GLASS KNIVES

(75) Inventors: Reinhardt Lihl; Anton Lang, both of Vienna (AT)

(73) Assignee: Leica AG, Vienna (AT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/804,540

(22) Filed: Feb. 24, 1997

(30) Foreign Application Priority Data

Feb. 23, 1996 (DE) .............................. 196 06 653

(51) Int. Cl.[7] .................................. C03B 33/033
(52) U.S. Cl. .............. 225/2; 225/96.5; 225/104; 269/902
(58) Field of Search .................. 225/96.5, 104, 225/1, 2, 94, 96, 97, 103, 105; 83/879, 880, 884, 886, 466; 269/63, 64, 902; 125/23.01, 23.02

(56) References Cited

U.S. PATENT DOCUMENTS

| | | | |
|---|---|---|---|
| 3,049,032 | * 8/1962 | Schabot | 269/900 X |
| 3,207,398 | * 9/1965 | Forsstrom et al. | 225/96 |
| 3,494,521 | * 2/1970 | Hellstrom | 225/96.5 |
| 3,657,791 | * 4/1972 | Hobbs | 225/96.5 X |
| 3,908,878 | * 9/1975 | Blum | 225/96.5 |
| 4,436,385 | * 3/1984 | Fischer et al. | 269/902 X |
| 5,044,245 | * 9/1991 | Molleker et al. | 83/886 |
| 5,174,188 | * 12/1992 | Petroz | 225/96 X |
| 5,219,107 | * 6/1993 | Persson | 225/103 X |
| 5,769,297 | * 6/1998 | Loomis et al. | 225/96.5 |

OTHER PUBLICATIONS

Balanced Break Glass Knifemaker, Leica Aktiengesellschaft, E–7/92, 1992.

"Reichert Knifemaker, Knifemaker for Symmetrical Breakage of Glass", 2.K.–Reichert EM–Laboratory–D–3/93, 1993.

* cited by examiner

Primary Examiner—Clark F. Dexter
(74) Attorney, Agent, or Firm—Foley & Lardner

(57) ABSTRACT

A device for forming two triangular glass knives from a glass square, such as for ultramicrotomy, has a rotary table and a holding device for receiving, aligning, and fixing the glass square to be broken positioned on the rotary table. The holding device has two opposingly arranged clamping jaws of U-shaped profile for holding the glass square therebetween arranged on the rotary table. The rotary table's axis of rotation is aligned with the center of the glass square held between the clamping jaws. A scoring and breaking device is positioned above the table alignable with the glass square.

11 Claims, 2 Drawing Sheets

DEVICE FOR FORMING TRIANGULAR GLASS KNIVES

BACKGROUND OF THE INVENTION

Triangular glass knives used for cutting in ultramicrotomy are typically produced by the user. This ensures that a high-quality triangular glass knife having a specific dimension and a specific cutting angle with respect to the specimen section is met according to its desired requirements.

The glass knives are produced from commercially available glass strips, for example, having a length of 400 mm. These glass strips are first repeatedly broken symmetrically until individual glass squares are obtained. The glass squares each are broken along the respective square diagonal so that two individual triangular glass knives with a cutting angle, for example, of 45° are formed.

It has been found that the glass squares do not break exactly along their angle bisector (e.g., 45°). Scoring and breaking the glass square along the angle bisector always leads to an uncontrolled breakage, forming an unusable or unacceptable triangular glass knife. For this reason, the glass square is not scored exactly along its angle bisector but slightly offset from it. In this arrangement, the score line intersects the diagonal in the center point of the square. This provides two individual triangular glass knives, each with a sharp edge suitable for cutting and a blunt break point.

An appliance that fulfills the production requirements of triangular glass knives of this kind is known from the LEICA publication Reichert Knifemaker, Knifemaker zum symmetrischen Glasbruch (translated Reichert Knifemaker, Knifemaker for Symmetrical Breakage of Glass), 2.K.-Reichert EM-Laboratory-D-3/93, 1993. This appliance has a scoring wheel arranged in a fixed location and a device provided in a fixed location for applying a breaking force. To hold the glass squares, the Reichert Knifemaker is equipped with two individual clamping jaws having a U-shaped profile, which are designed to be displaceable, independently of one another, laterally and parallel to one another. Adjustments are necessary to align the glass square beneath the scoring wheel and to set the required score line.

Due to the independent adjustability of the two clamping jaws and the required setting precision, making adjustments is relatively time-consuming. Adjustments have to be made every time, for example, when a different score angle is needed or the scoring wheel is changed. Readjustments are also necessary for glass strips that originate from different manufacturers.

Accordingly, there is a need for a device for forming triangular glass knives of the type described in the Reichert Knifemaker that provides simplified handling and yet precisely orients the glass squares. The present invention meets this need.

SUMMARY OF THE INVENTION

The present invention relates to a device for forming a triangular glass knife from a glass square, more particularly to a device for breaking the glass square into two triangular glass knives. The device includes a rotary table having an axis of rotation, a holding device, and a device for scoring and breaking the glass square. The holding device holds, aligns, and fixes the glass square relative to the scoring and breaking device. The holding device is positioned on the rotary table. Specifically, the holding device can have two opposed clamping jaws within which the glass square can be held. The rotary table's axis of rotation is aligned with the center of the glass square held by the jaws. The scoring and breaking device scores and breaks the glass square held between the clamping jaws into two triangular glass knives.

The jaws can have a U-shaped profile for receiving the glass square. The rotary table can include a handle for positioning the glass square held between the jaws. The handle can be a pivoted lever. An adjusting screw can be used to intercept the lever and position the turntable, which sets the glass square relative to the scoring device and the breaking device.

BRIEF DESCRIPTION OF THE DRAWINGS

These and other features, aspects, and advantages of the present invention will become more apparent from the following description, appended claims, and accompanying drawings, which are briefly described below.

DETAILED DESCRIPTION OF THE PREFERRED EMBODIMENTS

Figure 1:
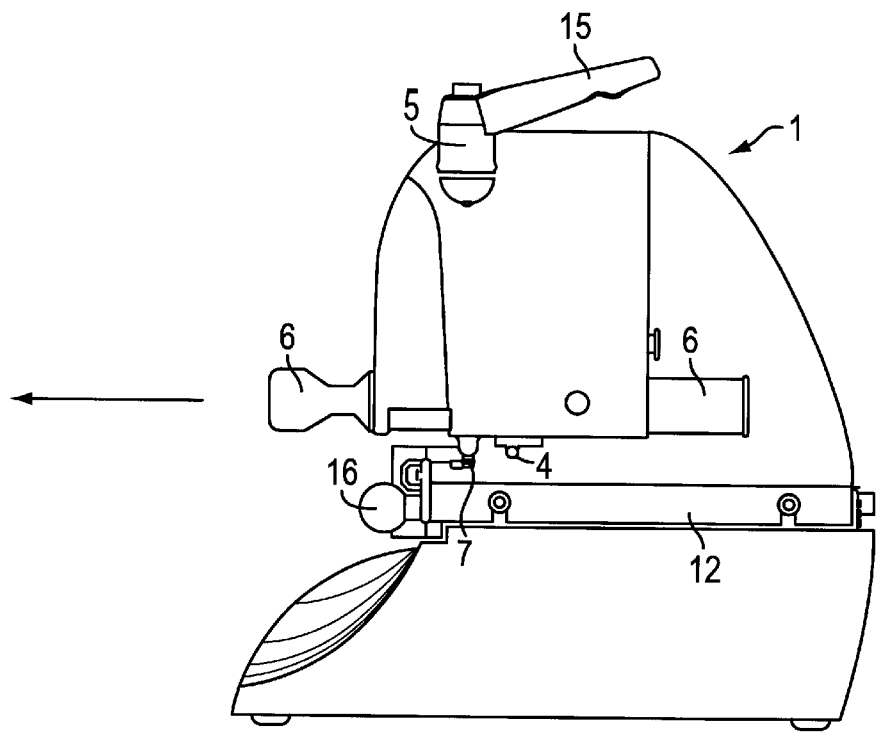
FIG. 1 shows a side view of a glass breaking appliance.

FIG. 1 shows a side view of a glass breaking appliance having a housing 1, a scoring wheel 4, and a breaking device 5. The breaking device 5 has a turning lever 15 connected to two breaking pins 7 via a rod (not shown) running in the interior of the housing 1. Using the turning lever 15, the breaking pins 7 can be applied to a glass square 2 with a defined force. The scoring wheel 4 is fixedly connected to a scoring rod 6. By pulling out the scoring rod 6 in the direction of the arrow, the scoring wheel 4 can be moved along the glass.

Furthermore, an adjustable stop bar 12 for the glass strips is provided on the housing 1. The stop bar can be moved into defined stop positions by means of a handle 16 to break the desired glass squares 2 out of the glass strips.

Figure 2:
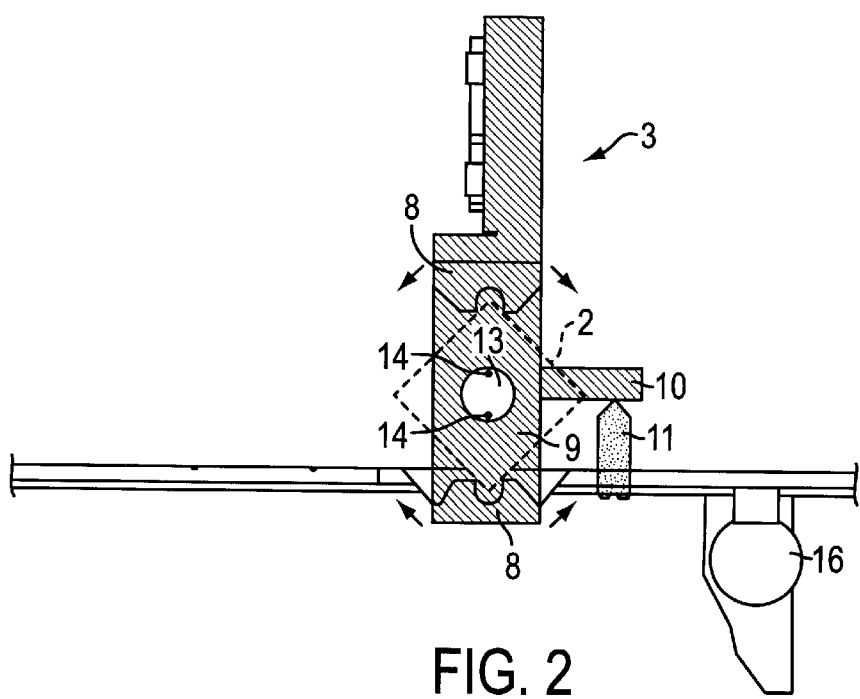
FIG. 2 shows a glass square holding device.

FIG. 2 shows a holding device 3 having two clamping jaws 8 of U-shaped profile for holding a glass square 2 to be broken. The complete holding device 3 is arranged on a rotary table 9, which is only indicated diagrammatically, designed to be rotationally movable in the direction of the arrows by means of a handle 10, which can be a pivoted lever and which can extend radially from the table. The rotary table 9 is mounted such that its fixed axis of rotation 13 lies in the center of the glass square 2. An adjusting screw 11 is aligned with the handle 10 for finely adjusting the position of the rotary table 9.

Furthermore, two fixed pressure pins 14 are arranged beneath the glass square 2 spaced from the axis of rotation 13. The pressure pins 14 are fixedly disposed within an opening at the rotational center of the rotary table 9 such that the rotary table is rotatable relative thereto. Further, the pressure pins 14 correspond to the two breaking pins 7, wherein the breaking pins 7 can be moved vertically by means of the lever 15 (FIG. 1) so that the pressure pins 14 and the breaking pins 7, which are aligned at least approximately at 90° to one another, provide for a breaking of the scored glass square 2. The score line produced by actuating the scoring rod 6 lies above and is generally aligned with the pressure pins 14.

After clamping the glass square 2 between the two clamping jaws 8, the glass square 2 can be aligned by means of the handle 10, with the adjusting screw 11, so that the score line runs in the vicinity of the diagonal of the glass square and intersects the diagonal along the axis of rotation 13. If the score line runs exactly along the diagonal, it would uncontrollably break the glass square, as described before.

Figure 3:
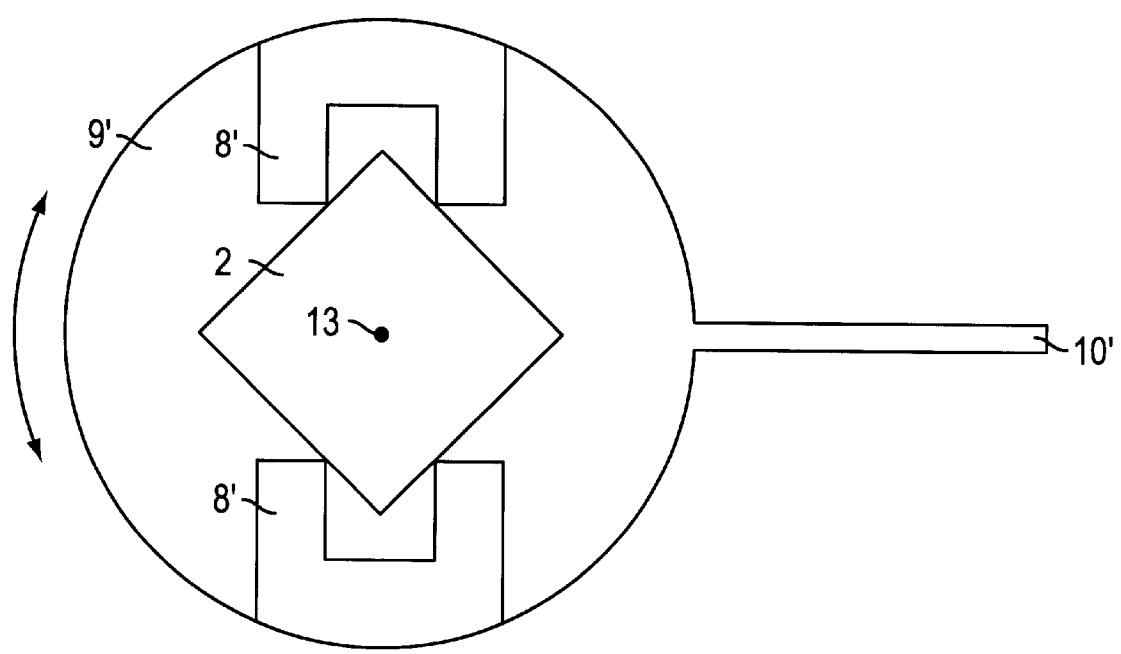
FIG. 3 shows an alternate embodiment with of the rotary table with a handle.

FIG. 3 shows an alternate embodiment with the rotary table 91 having two clamping jaws 81 arranged thereon holding the glass square 2. The handle 101 is fastened on the rotary table 91 so that the table 91 can be moved manually in the directions of the double arrow.

In this embodiment, the clamping jaws are of fixed design. It may be advantageous for one or both clamping jaws 81 to be resiliently mounted to securely clamp the glass square 2.

In the exemplary embodiment described, the glass squares are broken at an angle of approximately 45°. Other breaking angles can be contemplated using the present invention.

Given the disclosure of the present invention, one versed in the art would appreciate that there may be other embodiments and modifications within the scope and spirit of the present invention. Accordingly, all modifications attainable by one versed in the art from the present disclosure within the scope and spirit of the present invention are to be included as further embodiments of the present invention. The scope of the present invention accordingly is to be defined as set forth in the appended claims.

The disclosure of German priority application 19606653 filed Feb. 23, 1996, in its entirety, including the drawings, claims, and the specification thereof, is incorporated herein by reference.

We claim:

1. An apparatus for forming a triangular glass knife from a glass square, comprising:
    a rotary table having an axis of rotation;
    a holding device for holding, aligning, and fixing the glass square, the holding device having two opposed clamping jaws positioned on the rotary table for holding the glass square, wherein the jaws are positioned on opposite sides of the axis of rotation so that a centerpoint between the jaws coincides with the axis of rotation, whereby a center of the glass square placed in the jaws is aligned with the axis of rotation;
    a scoring device movably supported for movement across the rotary table for cutting a scoring line on the glass square held between the clamping jaws, the scoring device being aligned with the axis of rotation of the rotary table for movement along a line passing through the centerpoint between the jaws, for thereby cutting a scoring line through the center of the glass square; and
    a breaking device for breaking the glass square into two triangular glass knives, the breaking device comprising two movable breaking members positioned above the rotary table and two pressure members positioned within an opening through the rotational center of the rotary table so as to be stationary relative to the rotary table during rotation of the rotary table and so as to lie below the glass square, for applying force to the glass square while the glass square is on the rotary table to break the glass square into two glass knives.

2. An apparatus according to claim 1, wherein the two movable breaking members are spaced apart, one on each side of the axis of rotation of the rotary table, and the two pressure members are spaced apart, one on each side of the axis of rotation of the rotary table.

3. An apparatus according to claim 2, wherein the braking members and the pressure members comprise pins, and wherein a line through the breaking pins lies at an angle of approximately 90° to a line through the pressure pins.

4. An apparatus according to claim 1, further comprising means associated with the rotary table for selectively adjusting the rotational orientation of the rotary table with respect to the scoring device.

5. An apparatus according to claim 1, further comprising a handle attached to the rotary table for rotating the rotary table and thereby orienting the glass square with respect to the scoring device and the breaking device.

6. An apparatus according to claim 5, wherein the handle comprises a lever.

7. An apparatus according to claim 5, further including an adjusting screw aligned with the handle for setting a rotational adjustment of the rotary table.

8. An apparatus according to claim 7, wherein the clamping jaws comprise a U-shaped profile for holding the corners of the glass square.

9. An apparatus according to claim 8, wherein the clamping jaws are resiliently mounted on the rotary table.

10. A method for breaking a glass square into two triangular glass knives, comprising:
    placing a glass square onto a rotary table having an axis of rotation;
    fixing the glass square on the rotary table with a holding device for holding, aligning, and fixing the glass square, the holding device having two opposed clamping jaws positioned on the rotary table, and wherein the fixing step includes the clamping jaws holding the glass square, wherein the jaws are positioned on opposite sides of the axis of rotation so that a centerpoint between the jaws coincides with the axis of rotation, whereby a center of the glass square placed in the jaws is aligned with the axis of rotation;
    adjusting the rotational orientation of the glass square by selectively rotating the rotary table with respect to a scoring device for cutting a scoring line on the glass square held between the clamping jaws;
    aligning the scoring device with the axis of rotation of the rotary table and moving the scoring device along a line passing through the centerpoint between the jaws;
    cutting a scoring line through the center of the glass square with said moving of said scoring device; and
    breaking the glass square into two triangular glass knives with a breaking device comprising two moveable breaking members positioned above the rotary table and two pressure members positioned within an opening through the rotational center of the rotary table so as to be stationary relative to the rotary table during said rotating of the rotary table and so as to lie below the glass square, by moving the breaking members to apply force to the glass square positioned on the rotary table, the force pressing the glass square against the pressure members to break the glass square.

11. A method according to claim 10, wherein the adjusting is further carried out by providing an adjusting screw cooperating with the rotary table.

* * * * *